United States Patent
Kim et al.

(10) Patent No.: US 8,461,368 B2
(45) Date of Patent: Jun. 11, 2013

(54) PROCESS FOR PREPARING ORGANIC SILANE COMPOUNDS HAVING BETA-CYANO ESTER GROUP

(75) Inventors: No Ma Kim, Daejeon (KR); Jeong Min Ha, Daejeon (KR); Sung Soo Yoon, Daejeon (KR)

(73) Assignee: LG Chem, Ltd., Seoul (KR)

( * ) Notice: Subject to any disclaimer, the term of this patent is extended or adjusted under 35 U.S.C. 154(b) by 833 days.

(21) Appl. No.: 12/312,920

(22) PCT Filed: Dec. 3, 2007

(86) PCT No.: PCT/KR2007/006182
§ 371 (c)(1),
(2), (4) Date: Oct. 30, 2009

(87) PCT Pub. No.: WO2008/069515
PCT Pub. Date: Jun. 12, 2008

(65) Prior Publication Data
US 2010/0113812 A1    May 6, 2010

(30) Foreign Application Priority Data
Dec. 8, 2006    (KR) .................. 10-2006-0124951

(51) Int. Cl.
*C07C 7/02*    (2006.01)
(52) U.S. Cl.
USPC ........... 556/415; 556/416; 556/428; 556/437; 556/438; 556/463; 556/465; 556/487

(58) Field of Classification Search
USPC ................ 556/415, 416, 428, 437, 438, 463, 556/465, 487
See application file for complete search history.

(56) References Cited

U.S. PATENT DOCUMENTS

| | | | |
|---|---|---|---|
| 4,360,686 A | 11/1982 | Wang et al. | |
| 5,994,570 A | 11/1999 | Ogawa et al. | |

FOREIGN PATENT DOCUMENTS

| | | |
|---|---|---|
| EP | 1085022 A1 | 3/2001 |
| JP | 4-312594 A | 11/1992 |
| JP | 2002-060396 A | 2/2002 |
| JP | 2005-314325 A | 11/2005 |

*Primary Examiner* — Elvis O Price
(74) *Attorney, Agent, or Firm* — McKenna Long & Aldridge, LLP

(57) ABSTRACT

The present invention relates to a process for preparing organic silane compounds having a β-cyano ester group. In particular, the present invention relates to a process for preparing organic silane compounds having a β-cyano ester group, in which β-cyano β-cyano containing compounds having an unsaturated group are hydrosilylated using a hydro alkoxy silane in the presence of a platinum-vinyl siloxane catalyst. The preparation process according to the present invention can stably initiate and progress the reaction, minimize the generation of by-products, and prepare organic silane compounds having a β-cyano ester structure with high yield.

11 Claims, No Drawings

PROCESS FOR PREPARING ORGANIC SILANE COMPOUNDS HAVING BETA-CYANO ESTER GROUP

This application is a 35 U.S.C. §371 National Stage entry of International Application No. PCT/KR2007/006182, filed on Dec. 3, 2007, and claims the benefit of Korean Application No. 10-2006-0124951, filed on Dec. 8, 2006, both of which are hereby incorporated by reference in their entirety.

TECHNICAL FIELD

The present invention relates to a process for preparing organic silane compounds having a β-cyano ester group. In particular, the present invention relates to a process for preparing organic silane compounds having a β-cyano ester group, in which β-cyano ester containing compounds having an unsaturated group are hydrosilylated using a hydro alkoxy silane in the presence of a platinum-vinyl siloxane catalyst. The preparation process according to the present invention can stably initiate and progress the reaction, minimize the generation of by-products, and prepare organic silane compounds having a β-cyano ester structure with high yield.

BACKGROUND ART

A conventional process of preparing organic silane compounds is to cause hydrogenated silane containing compounds to react with unsaturated organic compounds in the presence of a catalyst, which is generally referred to as a hydrosilylation reaction. The hydrosilylation reaction is commonly carried out by successively adding hydro alkoxy silanes to unsaturated group containing organic compounds. A chloroplatinic acid catalyst (H2PtCl6 6H2O) as a catalyst for the hydrosilylation reaction is disclosed in Japanese Patent Laid-open Nos. (Sho) 63-250390, (Sho). 63-313793, and (Hei) 11-323132. However, in a case where the platinum chloride catalyst is used in the hydrosilylation reaction, there are problems in that it is difficult to remove the heat significantly generated during the initial reaction, and in a batch reaction system, each reaction is not constantly processed. Further, when a reaction temperature is increased so as to improve the reaction yield, the problem may arise that by-products are considerably generated.

DISCLOSURE

Technical Problem

The present invention is conceived to solve the aforementioned problems in the prior art. An object of the present invention is to provide a process for preparing silane compounds through a hydrosilylation reaction using unsaturated group containing organic compounds and hydro alkoxy silanes, wherein platinum-vinyl siloxane is used as a catalyst, a yield of a final product is high, reaction heat is easily removed, and the by-product generation is prevented.

Technical Solution

The present invention relates to a process for preparing a compound represented by the following Formula 3 by reacting a compound represented by the following Formula 1 with a compound represented by the following Formula 2 in the presence of a platinum-vinyl siloxane complex.

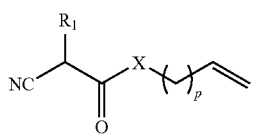

[Formula 1]

$HSi(OR_2)_n(R_3)_{3-n}$

[Formula 2]

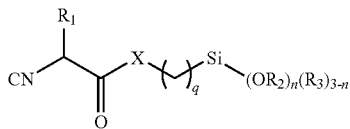

[Formula 3]

wherein,

R1 represents hydrogen or alkyl group of 1~3 carbon atoms,

X represents NR4, an oxygen atom or a sulfur atom,

R4 represents hydrogen or alkyl group of 1~3 carbon atoms, each R2 and R3 represents alkyl group of 1~6 carbon atoms independently, p is an integer ranging from 1 to 8, n is an integer ranging from 1 to 3, and q is an integer ranging from 3 to 10.

Hereinafter, a preparation process according to the present invention will be described in more detail.

In the preparation process of the present invention, the starting material is a β-cyano ester containing compound represented by the following Formula 1. The compound of Formula 1 has a double bond at its terminal end, and a terminal carbon atom of the double bond binds to a silane atom of the compound of Formula 2, to thereby prepare a target compound.

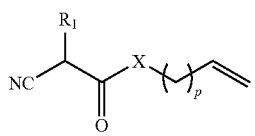

[Formula 1]

wherein,

R1 represents hydrogen or alkyl group of 1~3 carbon atoms, preferably hydrogen or methyl group, more preferably hydrogen;

X represents NR4, where R4 represents hydrogen or alkyl group of 1~3 carbon atoms, an oxygen atom or a sulfur atom, preferably NR4, where R4 represents methyl group, or an oxygen atom, more preferably oxygen atom; and p represents an integer ranging from 1 to 8, preferably 1 or 2, more preferably 1.

In the preparation process of the present invention, the reactant is a hydro alkoxy silane compound represented by the following Formula 2.

$HSi(OR_2)_n(R_3)_{3-n}$   Formula 2 wherein, each R2 and R3 represents alkyl group of 1~6 carbon atoms independently, preferably methyl group or ethyl group independently;

and n represents an integer ranging from 1 to 3, preferably 2 or 3.

The compound of Formula 2 may include trimethoxy silane, triethoxy silane, methyl dimethoxy silane, or dimethyl methoxy silane, but is not limited thereto.

In the preparation process of the present invention, the final target material is a hydro alkoxy silane compound represented by the following Formula 3.

[Formula 3]

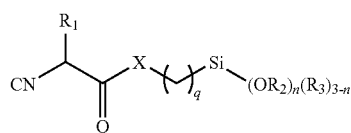

wherein,

R1, R2, R3, X and R4 are the same as defined in Formulae 1 and 2, respectively; and q is an integer ranging from 3 to 10, preferably 3 or 4, more preferably 3.

The compound of Formula 3 is preferably a compound represented by the following Formula 4 or 5.

[Formula 4]

[Formula 5]

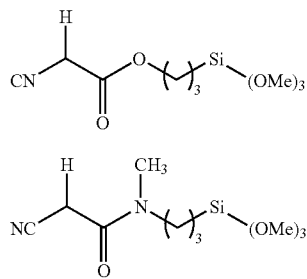

The compound of Formula 3 can be used for various purposes, for example, of enhancing the affinity between an organic resin and an inorganic filler, or improving the adhesiveness between a coating layer composed of a matrix, resin and a substrate. The compound of Formula 3 is particularly suitable for being used as a silane coupling agent of an acrylic resin composition, a thermosetting resin composition, or a thermoplastic resin composition.

In the process for preparing the compound of Formula 3 by reacting the compound of Formula 1 with the compound of Formula 2 according to the present invention, a platinum-vinyl siloxane complex is used as a catalyst for a hydrosilylation reaction.

Vinyl siloxane as a coordinator for the platinum-vinyl siloxane complex is not limited to any particular one, but it is preferable to select the vinyl siloxane from a cyclic structure, an acyclic structure and a mixture thereof and to have 2 to 4 silicon atoms having a vinyl group. The vinyl siloxane may preferably include divinyl disiloxane, divinyl trisiloxane, divinyl tetrasiloxane, tetravinyl cyclo tetrasiloxane, or 1,3-divinyl-1,1,3,3,-tetramethylsiloxane, but are not limited thereto. Considering the object of the present invention, it is more preferable to use 1,3-divinyl-1,1,3,3,-tetramethylsiloxane.

Further, in the platinum-vinyl siloxane complex, there is no limitation to the number of the vinyl group which is coupled to the silane atom coordinating with platinum, but it is preferable to use the complex prepared by reacting 2 molecules of divinyl siloxane with 1 platinum atom.

Meanwhile, in the platinum-vinyl siloxane complex, the atomic value of platinum is preferably 0, but it is also permissible to use divalent or tetravalent platinum. The platinum-siloxane complex may be used in the form of dissolving or dispersing in a reaction solution, or being supported to an inorganic carrier such as activated carbon, silica gel or alumina.

In the preparation process of the present invention, the reaction condition is implemented by the following.

In the present invention, a reaction ratio of the compound of Formula 2 to the compound of Formula 1 is preferably 1:0.8 to 1.2 moles, more preferably 1:0.9 to 1.1 moles in terms of the economical efficiency and the prevention of by-products generation.

Further, the used amount of the platinum-siloxane complex is preferably in the range of $1 \times 10-6$ to $1 \times 10-3$ moles, more preferably in the range of $3 \times 10-6$ to $100 \times 10-6$ moles based on one mole of the compound of Formula 1. The reaction rate is too slow if the used amount of the catalyst is too small, wheareas it is economically unfavorable or a large quantity of by-products is generated if the amount thereof is too large.

Further, in the preparation process of the present invention, a reaction temperature is preferably in the range of 60 to 100° C., more preferably in the range of 70 to 90° C. Its reaction yield is remarkably decreased if the reaction temperature is too low, whereas the generation of by-products is significantly increased if the reaction temperature is too high. In the present invention, a reaction pressure may be normal pressure or high pressure, but there is no specific limitation.

Meanwhile, there is no limitation in the introduction of reaction materials in the present invention, but since the silylation reaction is an exothermic reaction, it is preferable to drop hydroxyl alkyl silane of Formula 2 at a proper rate in the presence of β-cyano ester of Formula 1 containing unsaturated group and the platinum-vinyl siloxane catalyst.

Further, the preparation process of the present invention does not require any specific reaction solvent, but various solvents including aromatic solvent such as toluene or xylene, aliphatic solvents, such as hexane or heptane, or the like may be used according to the purpose.

The reaction system is charged with inert gas such as nitrogen or argon to prevent the admixture of moisture, and during the reaction it is preferable to seal the reaction system with the same kind of the gas. Further, in order to prevent the admixture of moisture into the reaction system, it is preferable to use β-cyano ester compound of Formula 1 containing unsaturated group which has a low moisture content, and it is more preferable to use the same dehydrated. In this case, conventional dehydration methods, for example, azeotropic dehydration using various kinds of dehydrating agents or solvents, may be selected.

Hereinafter, preferred examples will be described to help to understand the present invention, but are only for illustrative purposes and not intended to limit the scope of the present invention.

EXAMPLE 1

An 1 L four-neck glass flask reactor sufficiently charged with nitrogen was equipped with a dropping funnel, a condenser and a thermostat, 127 g (1 mol) of dehydrated allyl cyanoacetate and 0.25 g ($10 \times 10-6$ mole platinum atom) of a xylene solution (3% solution) of a platinum-1,3-divinyl-1,1,3,3-tetramethyldisiloxane complex were added thereto, and then, the mixture was kept at a temperature of 72° C. The temperature of the reaction system was increased to 77° C. as soon as 122 g (1 mol) of trimethoxy silane was injected through the dropping funnel. Trimethoxy silane was injected for 3 hours while maintaining the temperature of the reaction system not to exceed 80° C. by regulating the injection rate of trimethoxy silane. Even after the injection of trimethoxy silane was completed, the reaction was continuously progressed until the temperature of the reaction system was decreased to 72° C. After the reaction was completed, the reaction mixture was analyzed with gas chromatography (GC). As a result, it has been found that allyl cyano acetate is completely consumed, and the yield of β-cyano acetopropyl trimethoxysilane obtained as a final product is about 80%.

The prepared cyanoacetoxypropyl trimethoxysilane was a colorless liquid, and its NMR analysis results are as follow:
1H NMR(CDCl3, 300 MHz):0.70(t, 2H), 1.83(p, 2H), 3.50 (s, 2H), 3.61(s, 9H), 4.22(t, 2H) 13C NMR(CDCl3, 300 MHz):4.6, 21.4, 24.0, 49.9, 67.9, 113.3, 163.1

EXAMPLE 2

A 1 L four-neck glass flask reactor sufficiently charged with nitrogen was equipped with a dropping funnel, a condenser and a thermostat, 127 g (1 mol) of dehydrated allyl cyanoacetate and 0.18 g of xylene solution of a platinum-1,3-divinyl-1,1,3,3-tetramethyldisiloxane complex (3% solution) (7×10−6 mole platinum atom) were added thereto, and then, the mixture was kept at a temperature of 72° C. The temperature of the reaction system was increased to 75° C. as soon as 122 g (1 mol) of trimethoxy silane was injected through the dropping funnel. Trimethoxy silane was injected for 3 hours while maintaining the temperature of the reaction system not to exceed 80° C. by regulating the injection rate of trimethoxy silane. Even after the injection of trimethoxy silane was completed, until the temperature of the reaction system was decreased to 72° C., the reaction was continuously progressed. After the reaction was completed, the reaction mixture was analyzed with gas chromatography (GC). As a result, it has been found that allyl cyano acetate is completely consumed, and the yield of β-cyano acetopropyl trimethoxysilane obtained as a final product is about 87%.

COMPARATIVE EXAMPLE 1

A 1 L four-neck glass flask reactor sufficiently charged with nitrogen was equipped with a dropping funnel, a condenser and a thermostat, 127 g (1 mol) of dehydrated allyl cyanoacetate and 0.2 g (10×10−6 mole platinum atom) of a chloroplatinic acid (H2PtCl6) iso-propanol solution were added thereto, and then, the mixture was kept at a temperature of 72° C. Trimethoxy silane 122 g (1 mol) was injected to the flask through the dropping funnel. During the injection, the temperature of the reaction system was maintained at 72° C. for a while, but increased up to about 90° C. due to a sudden generation of heat. Even after the injection of trimethoxy silane was completed, the reaction was continuously progressed until the temperature of the reaction system was decreased to 72° C. After the reaction was completed, the reaction mixture was analyzed with gas chromatography (GC). As a result, it has been found that a considerable amount of allyl cyano acetate is remained, by-products whose ingredients are difficult to be analyzed are largely generated, and the yield of β-cyano acetopropyl trimethoxysilane obtained as a final product is about 13%.

COMPARATIVE EXAMPLE 2

A 1 L four-neck glass flask reactor sufficiently charged with nitrogen was equipped with a dropping funnel, a condenser and a thermostat, 127 g (1 mol) of dehydrated allyl cyanoacetate and 10 g (500×10−6 mole platinum atom) of a chloroplatinic acid (H2PtCl6) iso-propanol solution were added thereto, and then, the mixture was kept at a temperature of 40° C. The temperature of the reaction system was increased to 55° C. when 122 g (1 mol) of trimethoxy silane was injected through the dropping funnel. After the injection of trimethoxy silane was stopped and the temperature of the reaction system was decreased to 40° C., trimethoxy silane was injected for 5 hours while the temperature of the reaction system was regulated not to exceed 50° C. After the reaction was completed, the reaction mixture was analyzed with gas chromatography (GC). As a result, it has been found that a considerable amount of allyl cyano acetate is remained, by-products whose ingredients are difficult to be analyzed are largely generated, and the yield of β-cyano acetopropyl trimethoxysilane obtained as a final product is about 35%.

COMPARATIVE EXAMPLE 3

The experiment was conducted according to the same process as described in Example 1 except that the reaction temperature was maintained to a range of 100 to 110° C. As the reaction was in progress, the viscosity of the reaction system was gradually increased. As a result of gas chromatography (GC) analysis, it has been found that allyl cyano acetate was completely consumed, but the yield of β-cyano acetopropyl trimethoxysilane obtained as a final product is about 20%, and a considerable amount of by-products whose ingredients are difficult to be analyzed are generated.

Advantageous Effects

The preparation process of the present invention can stably initiate and progress the reaction, minimize the generation of by-products, and prepare organic silane compounds having a β-cyano ester structure with high yield.

The invention claimed is:
1. A process for preparing a compound represented by the following Formula 3 by reacting a compound represented by the following Formula 1 with a compound represented by the following Formula 2 in the presence of a platinum-vinyl siloxane complex:

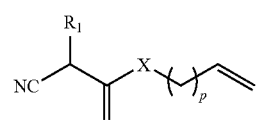

[Formula 1]

[Formula 2]

$HSi(OR_2)_n(R_3)_{3-n}$

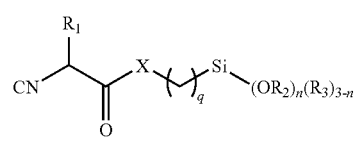

[Formula 3]

wherein,
$R_1$ represents hydrogen or alkyl group of 1~3 carbon atoms,
X represents $NR_4$, an oxygen atom or a sulfur atom,
$R_4$ represents hydrogen or alkyl group of 1~3 carbon atoms,
$R_2$ and $R_3$ represent alkyl group of 1~6 carbon atoms, independently,
p is an integer ranging from 1 to 8, n is an integer ranging from 1 to 3, and
q is an integer ranging from 3 to 10.

2. The process as claimed in claim 1, wherein $R_1$ represents hydrogen or methyl group,
X represents $NR_4$ or an oxygen atom,
$R_4$ represents methyl group,
$R_2$ and $R_3$ represent methyl group or ethyl group independently,
p is 1 or 2,
n is 2 or 3, and
q is 3 or 4.

3. The process as claimed in claim 2, wherein $R_1$ represents hydrogen,
X represents an oxygen atom,
$R_2$ and $R_3$ are methyl group or ethyl group, independently,
p is 1,
n is 2 or 3, and
q is 3.

4. The process as claimed in claim 1, wherein the compound of Formula 2 is trimethoxy silane, triethoxy silane, methyl dimethoxy silane, or dimethyl methoxy silane.

5. The process as claimed in claim 1, wherein the compound of Formula 3 is a compound represented by the following Formula 4 or 5:

[Formula 4]

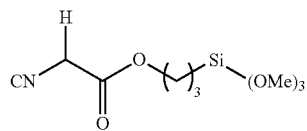

[Formula 5]

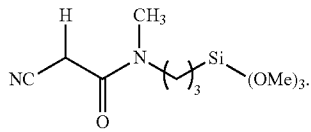

6. The process as claimed in claim 1, wherein the vinyl siloxane is selected from the group consisting of a cyclic structure, an acyclic structure and a mixture thereof, and contains 2 to 4 silane atoms having a vinyl group.

7. The process as claimed in claim 6, wherein the vinyl siloxane includes divinyl disiloxane, divinyl trisiloxane, divinyl tetrasiloxane, tetravinyl cyclo tetrasiloxane, or 1,3-divinyl-1,1,3,3,-tetramethylsiloxane.

8. The process as claimed in claim 1, wherein a reaction ratio of the compound of Formula 2 to the compound of Formula 1 is in the range of 1:0.8 to 1.2 moles.

9. The process as claimed in claim 1, wherein amount of the platinum-siloxane complex is $1\times10^{-6}$ to $1\times10^{-3}$ moles based on 1 mole of the compound of Formula 1.

10. The process as claimed in claim 1, wherein the reaction is performed at a temperature of 60 to 100° C.

11. The process as claimed in claim 1, wherein the compound of Formula 2 is dropped in the presence of the compound of Formula 1 and platinum-vinyl siloxane complex.

* * * * *